United States Patent [19]

Crowther

[11] Patent Number: 5,044,364
[45] Date of Patent: Sep. 3, 1991

[54] METHOD AND APPARATUS FOR FLOWING CONDITIONED AIR ONTO PERSON

[75] Inventor: Jonathan M. Crowther, Wilmington, Del.

[73] Assignee: Primed Products, Inc., Wilmington, Del.

[21] Appl. No.: 368,182

[22] Filed: Jun. 19, 1989

[51] Int. Cl.⁵ .................................................. A61F 7/00
[52] U.S. Cl. ................................ 128/400; 219/212; 128/373; 128/376
[58] Field of Search .............. 128/399, 400, 373, 379, 128/367–369, 376; 219/212; 4/535–537; 62/259.3; 165/46; 5/482, 485

[56] References Cited

U.S. PATENT DOCUMENTS

| | | |
|---|---|---|
| 1,980,516 | 11/1934 | Gail . |
| 2,093,834 | 9/1937 | Gaugler . |
| 2,104,587 | 1/1938 | Gaugler . |
| 2,512,559 | 6/1950 | William ..................................... 5/482 |
| 2,563,399 | 8/1951 | Doane . |
| 2,579,964 | 12/1951 | Reynolds . |
| 2,601,189 | 6/1952 | Wales, Jr. . |
| 2,998,817 | 9/1951 | Armstrong ......................... 128/400 |
| 3,444,922 | 5/1969 | Dingman . |
| 3,710,791 | 1/1973 | Deaton . |
| 3,844,339 | 10/1974 | Kranz ..................................... 165/46 |
| 3,890,019 | 10/1974 | Smirnov et al. ..................... 128/400 |
| 4,121,571 | 10/1978 | Pickering ............................ 128/400 |
| 4,136,413 | 1/1979 | Scales . |
| 4,183,184 | 1/1980 | Sargent . |
| 4,572,188 | 2/1986 | Augustine et al. ................... 128/380 |
| 4,660,388 | 4/1987 | Green, Jr. ............................. 165/46 |
| 4,867,230 | 9/1989 | Voss ..................................... 128/402 |

FOREIGN PATENT DOCUMENTS 113420  7/1984  European Pat. Off. ............ 128/400

Primary Examiner—Edward M. Coven
Assistant Examiner—Mark S. Graham
Attorney, Agent, or Firm—Connolly and Hutz

[57] ABSTRACT

A flexible treatment cover flows conditioned air onto a person positioned under the cover to assist in maintaining proper body temperature. The treatment cover has an inflated in use position above and out of contact with such person and a deflated flat stored position. Generally, the cover comprises a plurality of arch shaped air pockets fabricated of flexible material and connected together in series adjacent one another. Openings between adjacent air pockets allow inflation air to flow from one pocket to the next until the pockets are fully inflated. A separate air chamber on the underside of the cover has perforations which allow conditioned air to continuously flow out of the chamber onto the person under the cover. Air is supplied to inflate the air pockets and to continuously supply conditioned air to the air chamber.

18 Claims, 6 Drawing Sheets

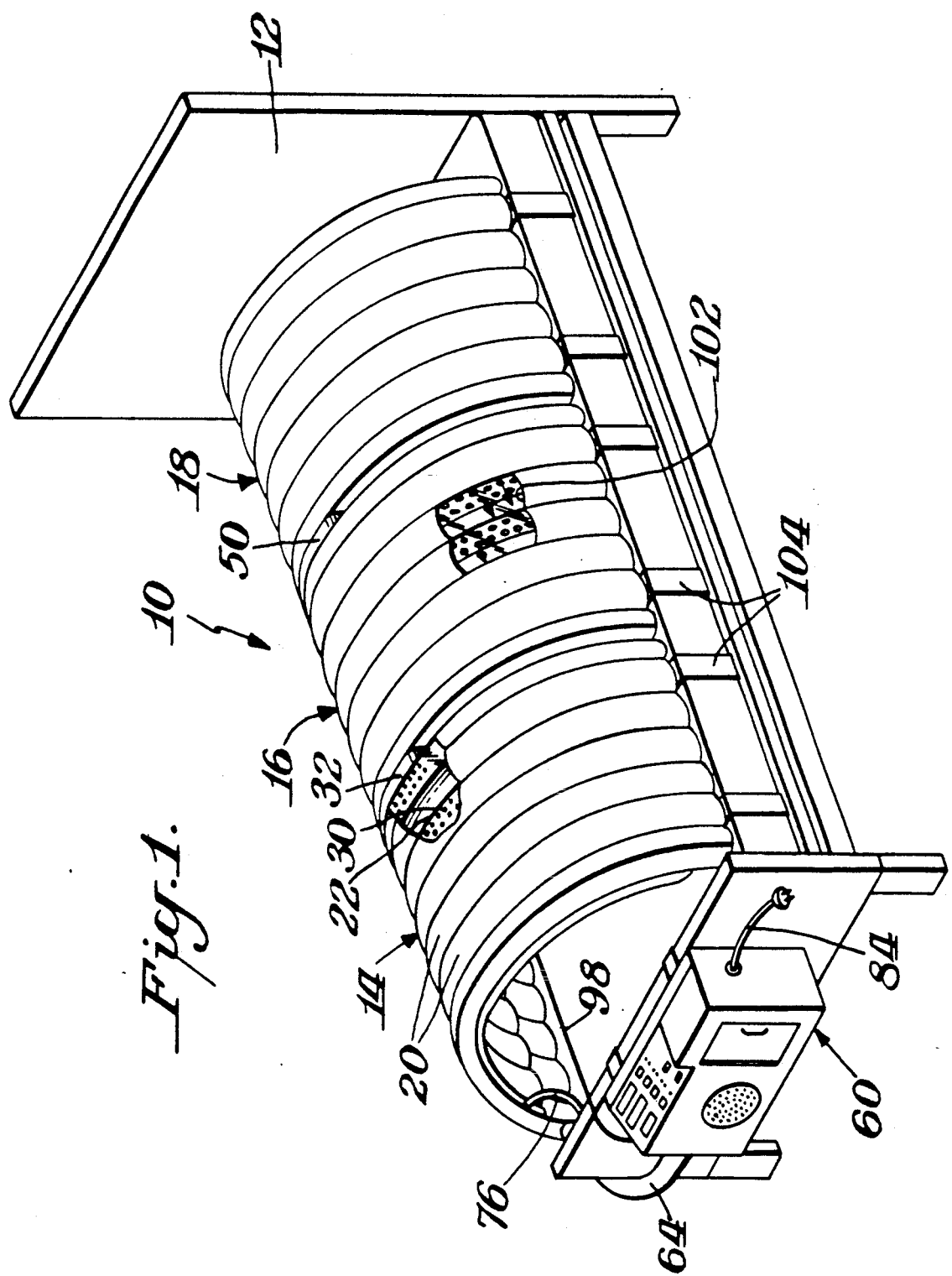

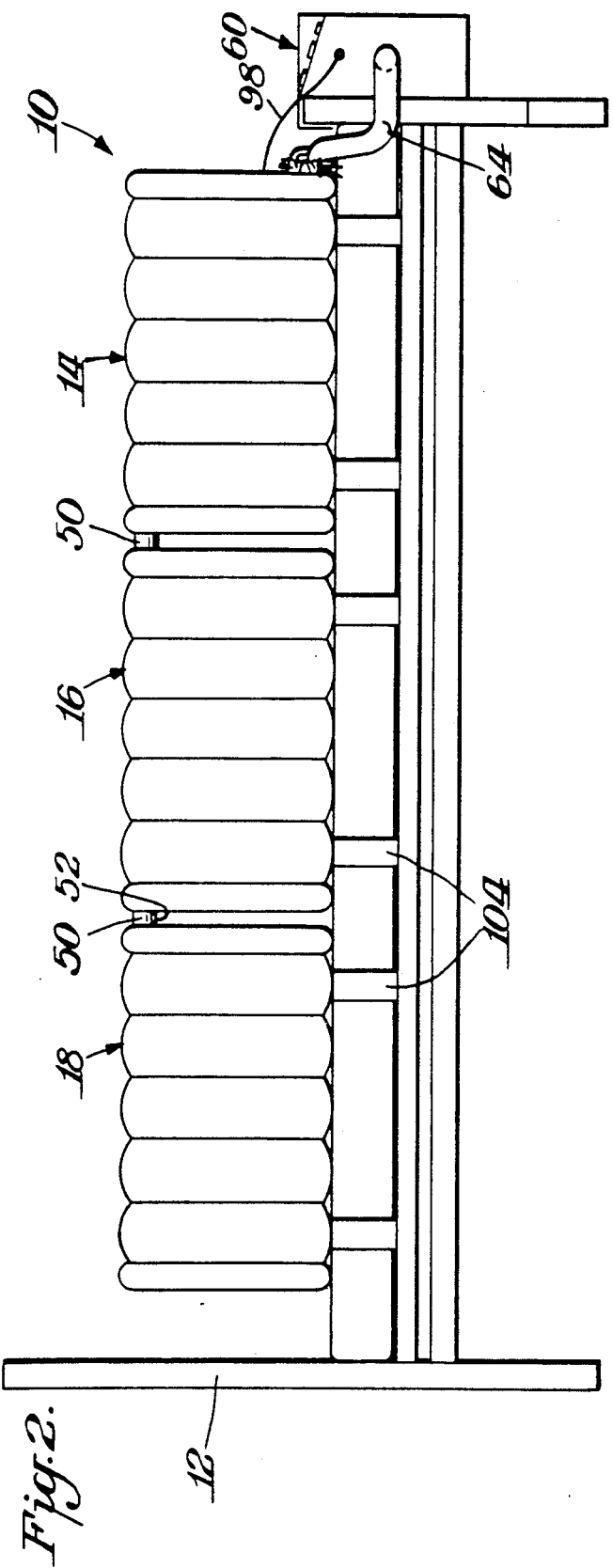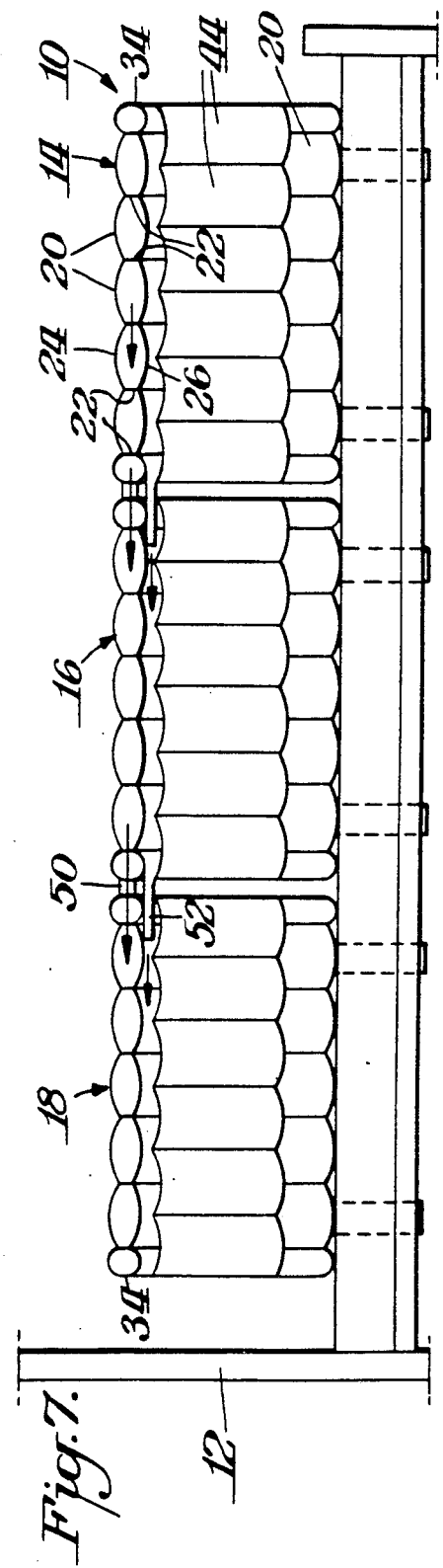

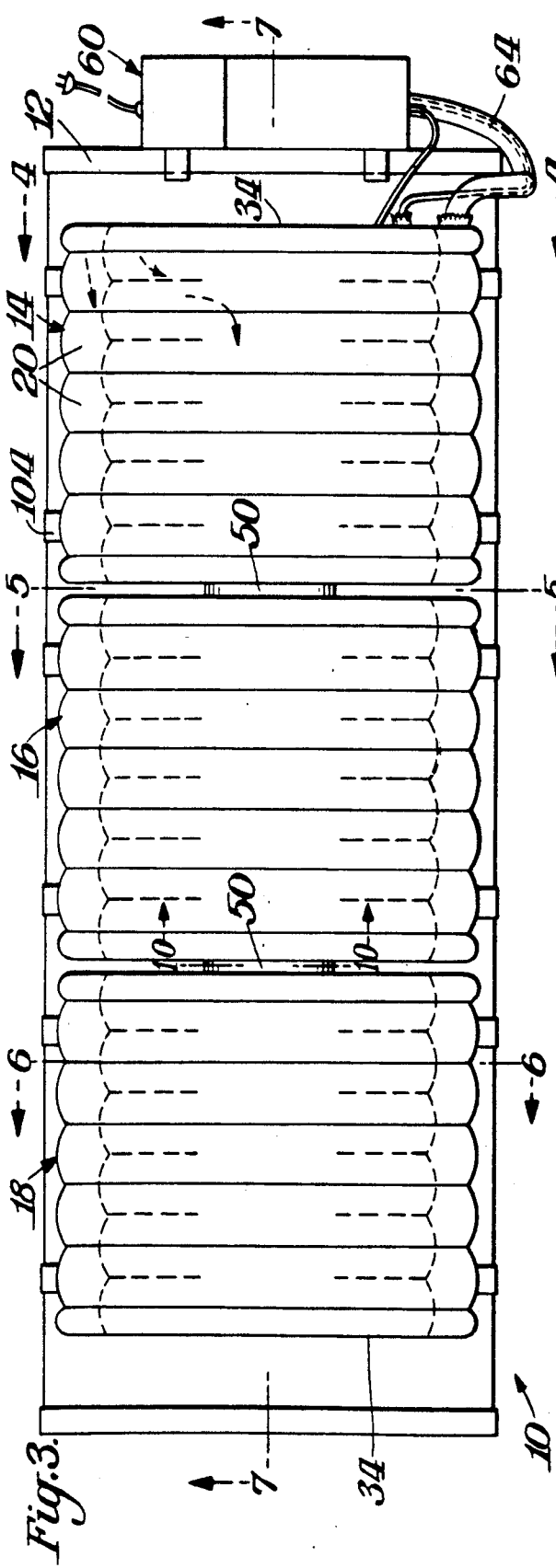
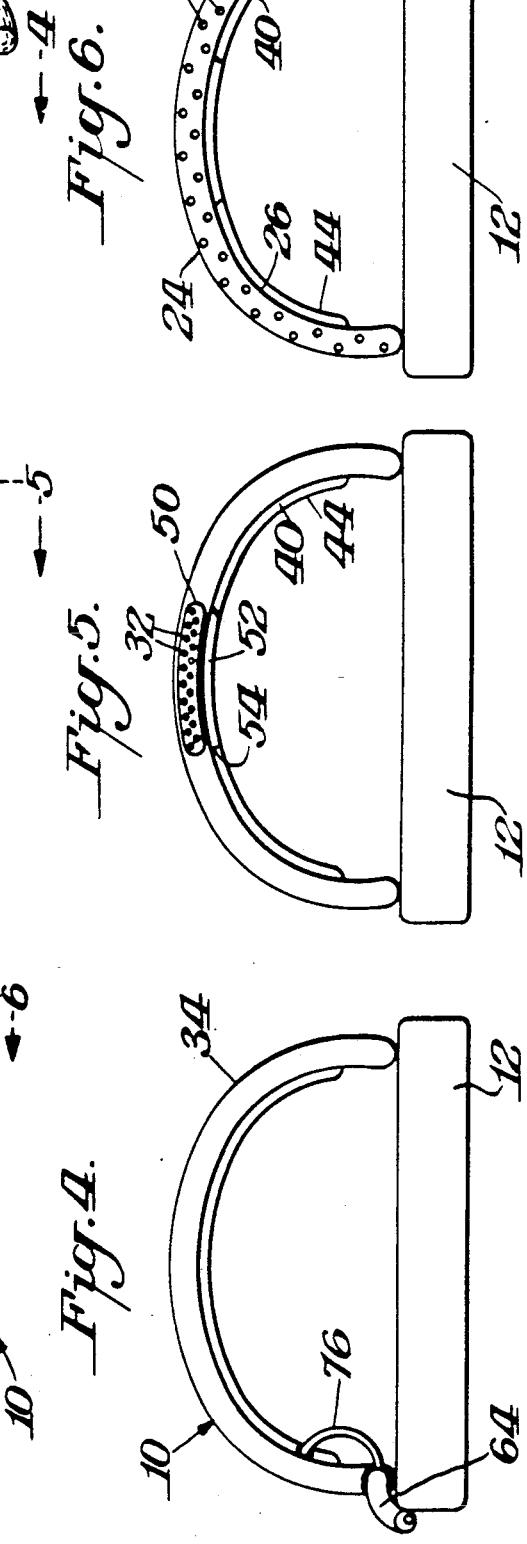

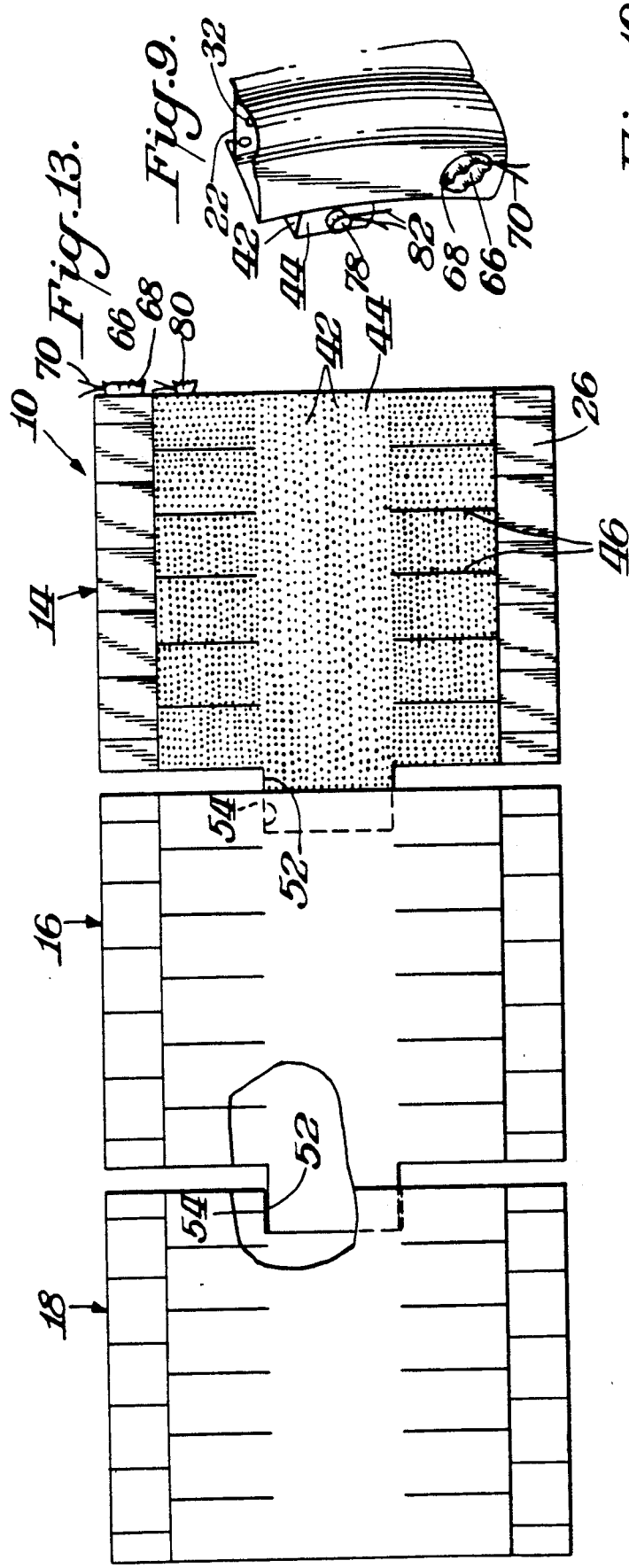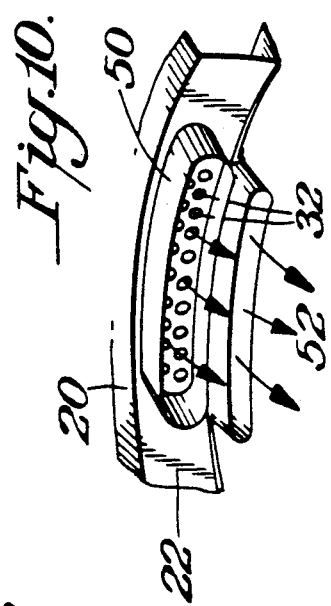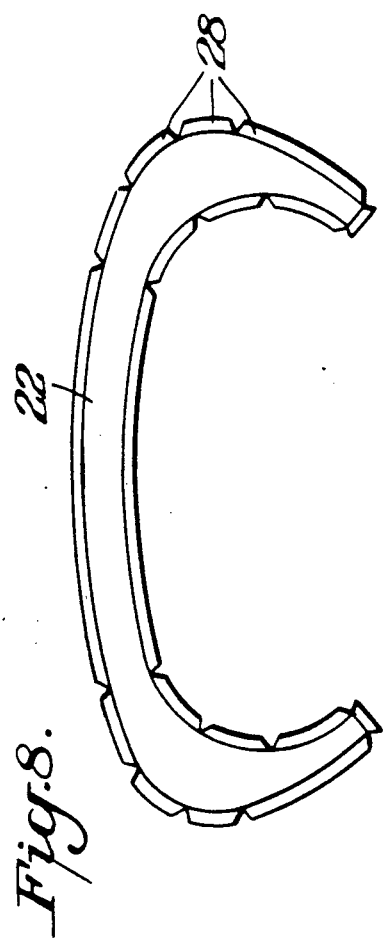

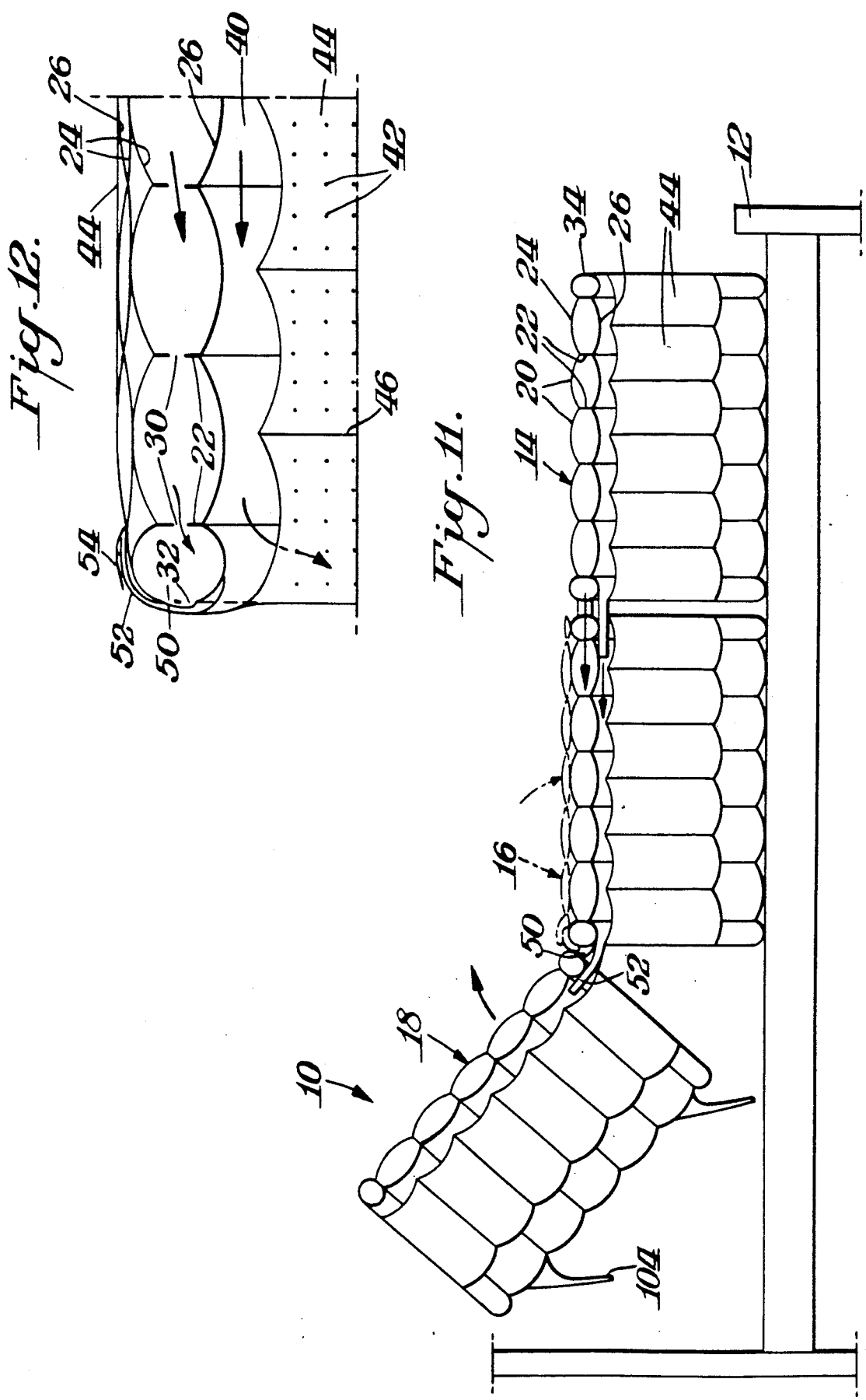

METHOD AND APPARATUS FOR FLOWING CONDITIONED AIR ONTO PERSON

BACKGROUND OF THE INVENTION

The present invention relates to an inflated treatment cover and to a method of treatment that includes flowing conditioned air onto a person from a cover suspended above and out of contact with the person to assist in maintaining proper body temperature.

Prior to the present invention, numerous procedures and devices have been proposed for treating persons having difficulty in maintaining a constant and proper body temperature. Burn patients, neurologically damaged individuals, neonatal patients, and other cases involving hypo-hyperthermia are but a few examples of situations where body temperature control is critical. Lives are lost when hospitalized patients fail to regulate their own body temperatures particularly when these temperatures rise above 106° F. or drop below 90° F.

When a patient suddenly loses control and his body temperature drops at an alarming rate, heat lamps are commonly used to warm the patient and thereby avoid a crisis situation. However, these lamps clutter the area and make the entire hospital room uncomfortably hot thereby making it quite difficult for doctors and nurses to administer to the needs of the patient. Cooling a patient who requires such treatment usually involves packing ice under and around the patient to lower his body temperature. This procedure takes considerable time and effort in set-up as well as clean-up, and is somewhat inefficient since cold air tends to drop to the floor where it has little beneficial effect on the patient.

Presently available hypo-hyperthermia devices work with a liquid water or alcohol) as the transfer medium and a vinyl blanket with water passage ways as the temperature transfer device. The water must be heated and cooled by use of a heat pump and the pumped through the blanket.

Moreover, the medical industry has long recognized the need for a single device which is capable of both heating and cooling a patient particularly since many patients go back and forth from hot to cold when they lose control of their systems.

SUMMARY OF THE INVENTION

Accordingly, it is an object of the present invention to provide a highly efficient and extremely versatile inflated treatment cover which administers conditioned air to a person directly under the cover while remaining out of contact with such person.

Another object of the present invention is an inflated treatment cover which is portable, lightweight, disposable and tear resistant and which allows for the free flow of conditioned air onto and around a person while remaining out of contact with that person.

Another object of the present invention is an inflated treatment cover which may be stored in a deflated flat folded condition and which requires minimal effort in assembly to its in use inflated condition.

Still another object of the present invention is a method of treating a person having difficulty in maintaining a proper body temperature by flowing conditioned air onto that person.

In accordance with the present invention, a flexible treatment cover is provided for flowing conditioned air onto a person located under the cover. The treatment cover has an inflated in use position above and out of contact with such person as well as a deflated flat stored condition. The cover comprises a plurality of arch shaped air pockets fabricated of flexible material and connected together in series adjacent one another. Openings between adjacent air pockets allow inflation air to flow from one pocket to the next until the air pockets are fully inflated. A separate air chamber on the underside of the arch shaped air pockets is also fabricated of flexible material, and perforations on the underside of the air chamber allow conditioned air to flow out of the chamber onto the person located under the cover. Air is supplied for inflating the air pockets and for continuously supplying conditioned air to the separate air chamber.

The air supply includes cooling and heating devices for adjusting to a predetermined level the temperature of the conditioned air which is continuously supplied to the air chamber.

Preferably, each air pocket comprises spaced apart arch shaped side ribs, an underside surface and outside top surface, and the openings between adjacent pockets are located in the side ribs. The separate air chamber may include a perforated sheet secured around its periphery to the underside of the arch shaped air pockets. This perforated sheet may also be secured to the air pockets at other locations and preferably such perforated sheet is spaced approximately 1 to 2 inches from the underside of the air pockets.

In the preferred embodiment of the present invention the flexible treatment cover has three interconnected individual sections including a middle section and a pair of opposed opposite end sections. Each cover section comprises a plurality of the arch shaped air pockets. and each section has a separate perforated air chamber on the underside thereof that allows conditioned air to flow from that cover section onto the person positioned under the cover. The three air chambers are connected to one another whereby conditioned air from a single source is supplied to all of the chambers.

The three individual sections of the cover are also connected together at an uppermost crown portion thereof by connectors that extend between adjacent sections of the cover at the air pockets. The air chambers on the underside of the cover are interconnected directly below these connectors. All of these connectors are flexible whereby one cover section may be folded over and onto an adjacent section about the connector points. This folding action also folds the connectors flat thereby sealing off the flow of air between the sections.

Preferably, each cover section includes five central air pockets and two end air pockets, one at each end of the five central pockets. Each air pocket comprises spaced apart arch shaped side ribs, an underside surface and an outside top surface. The underside surfaces of the air pockets of each cover section may comprise a sheet of flexible material, and the outside top surfaces of these air pockets may also comprise a sheet of such material.

In use, the treatment cover is positioned over the person requiring treatment and the arch shaped air pockets are inflated to thereby position the cover over and out of contact with such person. Conditioned air is supplied to the underside air chambers of the treatment cover where it continuously flows through an array of perforations onto the person being treated. The temperature of the air supplied to the underside of the treatment cover is adjusted to a desired level prior to flowing over the person being treated. When not in use, the treatment cover is deflated to a flat stored and preferably folded condition.

The method of using the treatment cover may also include the periodic and continuous determination of the body temperature of the person being treated. The desired temperature level of the conditioned air is then set in response to that determined body temperature.

BRIEF DESCRIPTION OF THE DRAWING

Novel features and advantages of the present invention in addition to those noted above will become apparent to persons of ordinary skill in the art from a reading of the following detailed description in conjunction with the accompanying drawing wherein similar reference characters refer to similar parts and in which:

FIG. 1 is a perspective view of an inflated treatment cover positioned over a hospital bed, according to the present invention.

FIG. 2 is a side elevational view of the inflated treatment cover shown in FIG. 1;

FIG. 3 is a top plan view of the inflated treatment cover shown in FIGS. 1 and 2;

FIG. 4 is a cross-sectional view taken along line 4—4 of FIG. 3;

FIG. 5 is a cross-sectional view taken along line 5—5 of FIG. 2;

FIG. 6 is a cross-sectional view taken along line 6—6 of FIG. 3;

FIG. 7 is a longitudinal sectional view taken along line 7—7 of FIG. 3;

FIG. 8 is a front elevational view of flexible rib material which extends between spaced apart upper and lower sheets of the inflated treatment cover;

FIG. 9 is a fragmental pictorial view of two air intake openings, one for the conditioned treatment air and the other for the inflation air;

FIG. 10 is a cross-sectional view taken along line 10—10 of FIG. 3 illustrating one of the air connectors located between the three individual sections of the treatment cover;

FIG. 11 is a cross-sectional view similar to FIG. 7 illustrating a deflated end section of the treatment cover being folded over the middle section thereof;

FIG. 12 is an enlarged cross-sectional detailed view illustrating air sealing between the folded deflated end section and the middle section of the treatment cover;

FIG. 13 is a bottom plan view of the three sections of the treatment cover in deflated flat condition;

DETAILED DESCRIPTION OF THE INVENTION

Figure 14:
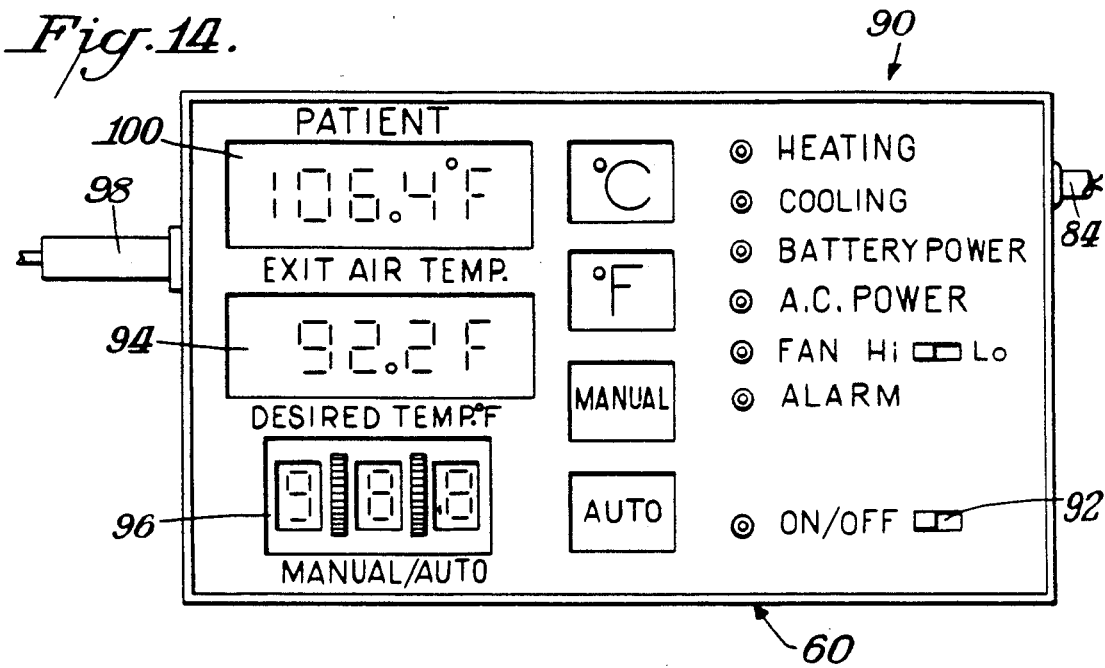
FIG. 14 is a top plan view of the control panel of the air supply unit.

Referring in more particularity to the drawing, FIGS. 1-3 illustrate an inflated treatment cover 10 for flowing conditioned air onto a person requiring assistance in maintaining a proper body temperature. In its inflated condition, treatment cover 10 is positioned over a hospital bed 12 where it is suspended above and out of contact with the person. Generally, the treatment cover includes three sections 14, 16, 18 connected together as explained more fully below. Each section is fabricated from flexible material which is lightweight and tear resistant and preferably disposable. Material such as TYVEK ® manufactured and sold by E.I.duPont de Nemours & Co. is a particularly satisfactory material for this purpose.

Treatment cover 10 includes support structure which functions to suspend the cover above and out of contact with the person positioned under the cover. The treatment cover also includes structure which functions to flow conditioned air onto the person being treated. As explained more fully below, the temperature of the conditioned air is controlled so as to assist the person in maintaining a constant and proper body temperature.

Cover sections 14, 16, 18 are generally identical in structure and function, and each section has support structure in the form of inflated components. Moreover, a manifold system operates to supply and flow conditioned air from the underside of the cover sections onto the person being treated. Each cover section includes a plurality of arch shaped air pockets 20 fabricated of flexible material and connected together in series adjacent one another. As shown, each cover section has five central air pockets with two additional air pockets, one at each end of the central pockets. The air pockets 20 are formed in part by spaced apart arch shaped side ribs 22 which are best shown in FIGS. 6 and 8. Construction of each air pocket is completed by an outside top surface 24 and an underside surface 26. Preferably, the top surfaces 24 of each treatment cover section comprise a single sheet of material and the underside surfaces 26 also comprise a single sheet of material. As can readily be understood, spaced apart side ribs 22 may be sewn or otherwise secured to these sheets in forming each treatment cover section. Peripheral tabs 28 on the side ribs facilitate such assembly.

The majority of the arch shaped side ribs 22 are perforated having openings 30 along the entire length thereof, as shown best in FIG. 6. These openings allow inflation air to flow from one air pocket 20 to the next until the treatment cover is fully inflated. The ribs adjacent the juncture between individual sections of the cover are not perforated throughout and instead only include a plurality of perforations 32 at the crown portion thereof where the individual sections are connected together. Ribs 34 at the extreme ends of the treatment cover do not include any perforations in order to prevent escape of the inflation air held inside air pockets 20. Otherwise, ribs 34 are identical to the other ribs 22.

The underside of each treatment cover section includes a separate air chamber 40 fabricated of flexible material and secured to the underside of the arch shaped air pockets 20. Each air chamber 40 has perforations 42 which allow conditioned air to flow from the chamber onto the person positioned under the treatment cover. As shown best in FIG. 13, each air chamber primarily comprises a sheet 44 of flexible material secured around its periphery to the underside of the arch shaped air pockets 20 by sewing or other means. Additionally, sheet 44 is secured &o the air pockets 20 along parallel lines 46 in such a manner that perforated sheet 44 is spaced approximately 1 to 2 inches from the air pockets. Perforated sheet 44 together with the underside of the air pockets produce air chamber 40, and the three air chambers of the cover collectively act as the above described manifold for receiving conditioned air and flowing that air through perforations 42 onto the person being treated.

Connection between the individual sections of treatment cover 10 is accomplished with a flexible sleeve-like connector 50 secured to the crown portion of the ribs 22 adjacent the juncture between these cover sections. Connector 50 is best shown in FIG. 10. As explained above, the end ribs 22 at the juncture between adjacent sections of the cover only include perforations 32 at the crown portion of those ribs. These perforations are surrounded by connector 50 whereby inflation air may travel from one section of the cover to an adjacent section through the perforations 32 and sleeve-like connector 50. Inflation air supplied to the cover is then free to travel from one pocket to the next through perforations 30 and then from one cover section to the next through perforations 32 and connectors 50.

The three air chambers 40 are also interconnected at the crown portion of the cover directly below connectors 50. In this regard, the air chamber positioned under cover section 14 has a long conduit piece 52 which bridges the gap between adjacent cover sections and which mates with an opening 54 in the air chamber of middle cover section 16. For reasons explained below, conduit piece 52 is slidably received in that opening 54 of the air chamber of the middle cover section. A similar connection is provided between the middle air chamber and the air chamber associated with cover section 18.

Figure 15:
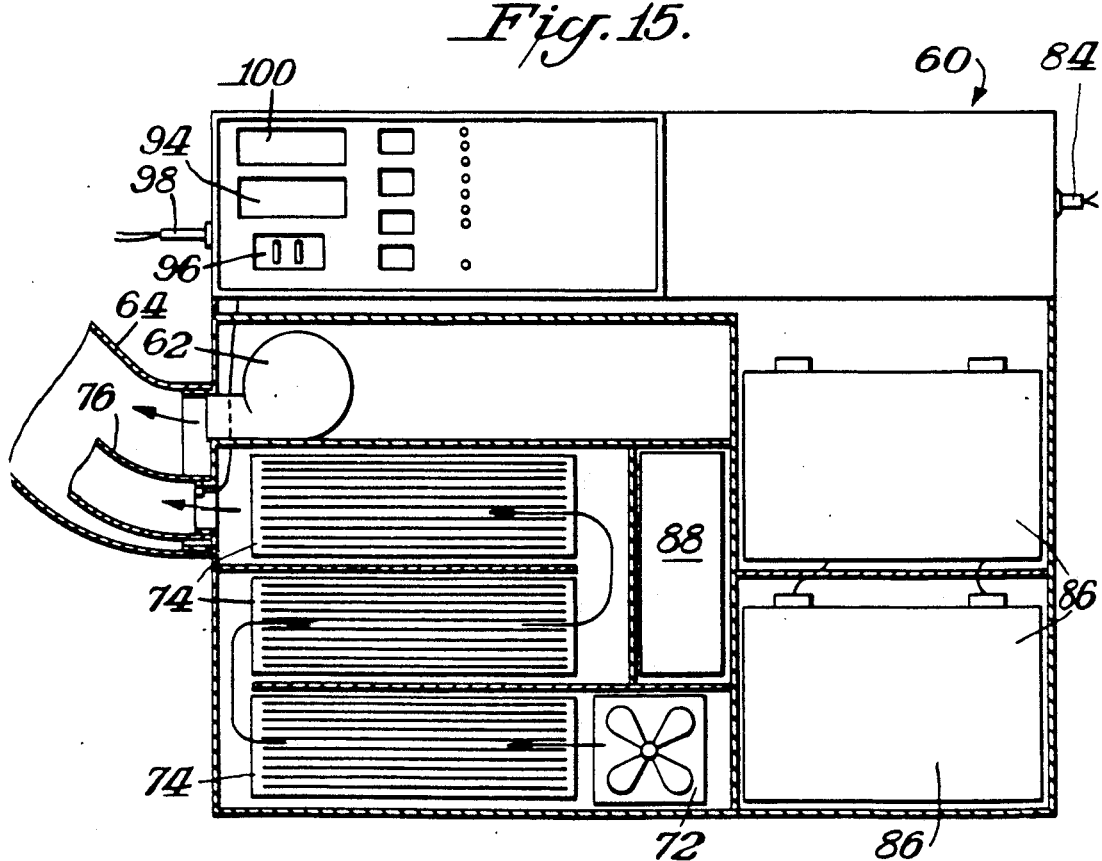
FIG. 15 is a partial sectional view of the air supply unit with portions of the cabinetry removed to show interior details.

Both inflation and conditioned air are delivered to the inflated treatment cover 10 by an air supply unit 60, shown best in FIGS. 14 and 15. Air necessary for inflating the individual air pockets 20 is generated by one or more blowers 62 in the unit. This blower is connected by a flexible hose 64 to an opening 66 in end rib 34 of cover section 14. Preferably, opening 66 is surrounded by an annular flange 68 of flexible material and a drawstring 70 to facilitate connection of hose 64 thereto.

Unit 60 also includes a fan 72 and series of heating and cooling units 74 through which air is blown by fan 72. Ultimately, air which is conditioned by the coolers and heaters exits unit 60 through a flexible hose 76 which is secured to air chamber 40 associated with cover section 14. An opening 78 in that air chamber is surrounded by an annular flange 80 of flexible material and a drawstring 82 to facilitate connection of hose 76 to the interconnected air chambers. The heaters and coolers 74 may comprise any one of a number of well known devices that function to heat and cool fluids such as air.

Air supply unit 60 is portable and runs on both ac and dc current. A suitable cord and plug 84 may be connected to any convenience outlet receptacle for supplying ac current to the unit. Additionally, the unit carries several storage batteries 86 and a battery charger 88. The batteries operate air supply unit when ac current is not available, primarily when a power failure occurs.

The air supply unit has a control panel 90 with an on-off control 92 for the unit. The panel displays the exit temperature 94 of the air supplied to the air chambers, and a control 96 is provided for selecting a particular temperature for that air. Once the desired temperature is selected, the coolers and heaters 74 function to produce and provide air having the selected temperature.

Another feature of the air supply unit 60 is a patient temperature probe 98 attached to the person under the treatment cover and a monitor 100 on the control panel which exhibits that temperature. Indicator lights are provided for heating, cooling, battery power, A.C. Power, alarm and fan. Operation of fan 72 may be either high or low.

As shown best in FIGS. 11 and 12, the overall length of inflated treatment cover 10 may be shortened if desired by simply folding end cover section 18 over and onto middle cover section 16. Since both air connections are located at the crown portion of the cover, a hinging action takes place about these connections.

Once cover section 18 is so manipulated, sleeve-like connector 50 positioned between cover sections 16, 18 is folded flat and thereby seals-off the flow of inflation air to the end cover section. Similarly, the connection 52,54 between the air chambers of the middle and end sections is folded flat thereby sealing-off the flow of conditioned air from the middle section to the end section. End section 18 simply deflates and rests upon middle section 16 in a flat condition. The remaining two sections of the treatment cover then function to provide the conditioned air. Such hinging action causes conduit piece 52 to slide relative to opening 54 but piece 52 has sufficient length whereby engagement in opening 54 is always maintained.

Use of one or two sections of the treatment cover may be particularly beneficial for infants or children when less overall length is necessary. Also, when administering to the needs of the person it is often necessary to fold end cover section 18 over middle section 16, as described above. It should also be understood that middle cover section 16 with the deflated end section 18 thereon may also be folded onto end section 14 of the cover if a single cover section is needed.

Viewing windows 102 may be provided in the cover so that the person can be observed throughout the treatment. In this regard, one or more of the air pockets 20 and portions of the air chamber 40 may be fabricated of transparent material to accomplish this result. Additionally, spaced apart tuck tabs 104 may be secured along the sides of each cover section for securing the treatment cover to the hospital bed 12. As shown in FIG. 1, these tabs are simply inserted under the mattress of the bed.

In use, the treatment cover 10 is positioned over the person on hospital bed 12 and the blower 62 is energized thereby causing inflation air to flow through hose 64 into the arch shaped air pockets 20 of end cover section 14. This air flows from one pocket to the next through the openings 30 in ribs 22. Such inflation air also flows to middle cover section 16 and end cover section 18 through the sleeve-like connectors 50 and the openings 32 in the end ribs. The air flow continues until all of the pockets are fully inflated and thereafter air only is supplied to compensate for leakage. This procedure positions the treatment cover above and out of contact with the person. The tuck tabs are used to anchor the cover in place.

After the desired temperature is established, conditioned air flows from hose 76 into the first of the three air chambers 40. Such flow continues from one chamber to the next through the connections 52, 54 between the air chambers. The conditioned air flows through the perforations 42 in the air chambers onto the person under cover 10 to thereby surround that person in an atmosphere of desired temperature to assist in maintaining a proper body temperature.

What is claimed is:
1. A flexible treatment cover for flowing conditioned air onto a person located under the cover having an inflated in use position above and out of contact with such person and a deflated flat stored condition comprising inflatable support means fabricated of flexible material having an upper surface portion and a lower surface portion, the inflatable support means having a generally arch shaped configuration when inflated, separate air chamber means secured to the lower surface portion of the inflatable support means fabricated of flexible material, the separate air chamber means having an underside surface with perforations therein which allow conditioned air to flow out of the chamber onto a person located under the cover, and air supply means for inflating the support means and for continuously supplying conditioned air to the separate air chamber.

2. A flexible treatment cover as in claim 1 wherein the air supply means includes cooling and heating means for adjusting the temperature of the conditioned air supplied to the separate air chamber means to a predetermined level.

3. A flexible treatment cover as in claim 1 wherein the flexible material from which the inflatable support means and separate air chamber means are fabricated is lightweight and tear resistant.

4. A flexible treatment cover as in claim 1 wherein the inflatable support means comprises a plurality of arch shaped air pockets connected together in series adjacent one another with openings between adjacent air pockets constructed and arranged to allow inflation air to flow from one pocket to the next until the pockets are inflated.

5. A flexible treatment cover as in claim 1 wherein the separate air chamber means includes a perforated sheet secured around its periphery to the lower surface portion of the inflatable support means.

6. A treatment cover as in claim 5 wherein the perforated sheet is also secured to the lower surface portion of the inflatable support means at other locations and wherein such perforated sheet is spaced approximately 1 to 2 inches therefrom.

7. A flexible treatment cover as in claim 1 wherein the cover has three interconnected individual sections including a middle section and opposite end sections, each section including said inflatable support means.

8. A flexible treatment cover as in claim 7 wherein the separate air chamber means includes an air chamber on the underside of each individual section of the cover having said perforations therein that allow air to flow out of the chambers, and means interconnecting the air chambers of the three interconnected sections of the treatment cover.

9. A flexible treatment cover as in claim 8 including connector means interconnecting the inflatable support means of the middle section of the cover to the inflatable support means of each of the opposite end sections.

10. A flexible cover as in claim 9 wherein the adjacent air chambers of the three individual sections of the cover are interconnected directly below the connector means.

11. A flexible cover as in claim 9 wherein the connecting means includes passageway therein extending between adjacent sections of the cover whereby inflation air flows between the individual cover sections.

12. A flexible cover as in claim 9 wherein the means interconnecting the air chambers and the connector means are flexible whereby one cover section may be folded over and onto an adjacent cover section about such interconnecting and connector means.

13. A flexible cover as in claim 12 wherein the means interconnecting the air chambers and the connector means are constructed and arranged to be folded flat when one cover section is folded over and onto an adjacent cover section about such interconnecting and connector means to thereby seal off air flow to the folded cover section.

14. A treatment cover a sin claim 7 wherein the air supply means is connected to directly supply inflation air to the inflatable support means of one of the two end cover sections and inflation air may flow from one section to the next to inflate the three cover sections.

15. A treatment cover as in claim 4 wherein the inflatable support means includes five central air pockets and two end air pockets, one at each end of the five central pockets, each air pocket comprising spaced apart arch shaped side ribs, an underside surface, and an outside top surface, the underside surfaces of the air pockets comprising the lower surface portion of the inflatable support means and the outside top surfaces of the air pockets comprising the upper surface portion of the inflatable support means.

16. A treatment cover as in claim 15 wherein the side ribs of each central air pocket include openings along the entire length thereof.

17. A flexible treatment cover as in claim 1 including window means for viewing a person under the cover.

18. A flexible treatment cover as in claim 1 including flexible tuck tabs connected to the inflatable support means and extending downwardly from the cover for securing the cover to a hospital bed.

* * * * *